United States Patent [19]

van Zorge

[11] 4,352,804

[45] Oct. 5, 1982

[54] OXIME ETHERS, THEIR PREPARATION AND PHARMACEUTICAL COMPOSITIONS CONTAINING THEM

[75] Inventor: Jacob A. van Zorge, Ameide, Netherlands

[73] Assignee: ACF Chemiefarma NV, Netherlands

[21] Appl. No.: 56,529

[22] Filed: Jul. 11, 1979

[30] Foreign Application Priority Data

Jul. 25, 1978 [GB] United Kingdom ............... 30952/78

[51] Int. Cl.$^3$ .................. A61K 31/495; C07D 241/12
[52] U.S. Cl. .............................. 424/250; 260/326.15; 424/251; 424/258; 424/270; 424/272; 424/273 R; 424/273 B; 424/274; 544/284; 544/237; 544/253; 544/283; 544/333; 544/334; 544/335; 544/336; 544/353; 544/354; 544/356; 544/405; 544/408; 544/409; 546/118; 546/141; 546/145; 546/153; 546/165; 548/179; 548/217; 548/327; 548/333; 548/336; 548/341
[58] Field of Search ....................... 544/336, 405, 409; 424/250

[56] References Cited

U.S. PATENT DOCUMENTS 3,205,234  9/1965  Schumann ............................ 546/333
3,957,805  5/1976  Fanshawe et al. ................... 544/336

FOREIGN PATENT DOCUMENTS 2800316  7/1978  Fed. Rep. of Germany .
1570082  4/1969  France .

OTHER PUBLICATIONS

Niemers, et al., "Synthesis", 1976, pp. 593–595.
Villani, et al., "J. Pharm. Sci.", vol. 58, 1969, p. 139.

Primary Examiner—Donald G. Daus
Assistant Examiner—James H. Turnipseed
Attorney, Agent, or Firm—Jacobs & Jacobs

[57] ABSTRACT

Oxime ether derivatives of the formula (I):

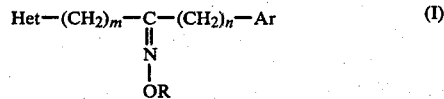

wherein Het is a monocyclic heteroaromatic group containing two hetero atoms at least one of which is nitrogen, or a bicyclic heteroaromatic group containing one or two hetero atoms at least one of which is nitrogen, Ar is a phenyl or a 5- or 6-membered monocyclic heteroaromatic group, and R is an alkyl, alkenyl, alkynyl, cyanoalkyl, carbamidoalkyl or aminoalkyl group, or N-oxides thereof, have anti-ulcer activity in the gastro-intestinal tract of mammals.

8 Claims, No Drawings

OXIME ETHERS, THEIR PREPARATION AND PHARMACEUTICAL COMPOSITIONS CONTAINING THEM

The invention relates to certain novel pharmacologically active oxime ether derivatives, to methods for their preparation, to pharmaceutical compositions containing such compounds as active ingredients and to certain novel intermediates.

In Farmaco, Ed. Sci. 19, 668–702 (1964), Chem. Abstr. 61, 10545e (1964),phenyl 2-pyridinyl ketone, O-dimethylaminoethyl oxime methiodide has been described, which compound showed acetylcholine antagonistic activity. The salts of the tertiary amine should possess papaverine-like activity in vitro.

In U.S. Pat. No. 3,205,234 a number of N-oxides of pyridinyl ketone O-hydrocarbon oximes have been mentioned, wherein the hydrocarbon group may be saturated or unsaturated acyclic aliphatic, cycloaliphatic, cycloaliphaticalkyl or araliphatic, containing up to twelve carbon atoms. The N-oxides are said to be active and useful as antiinflammatory agents and drug-potentiators (e.g. potentiation of barbiturate-induced sleep in mammals), although this statement has not been supported by any pharmacological data.

According to this reference, these N-oxides are prepared by reacting a corresponding pyridinyl ketone O-hydrocarbon oxime with a peroxide. The starting oxime ethers are only described as intermediates. Thus, no pharmacological activity of these compounds has been mentioned.

In U.S. Pat. No. 3,290,320, which corresponds to British Pat. No. 1,070,964, phenyl 2-pyridinyl ketone, O-di(m)ethylaminoethyl/propyl oximes have been described, which compounds showed anti-androgenic activity.

In J. Pharm. Sci. 58, 138–141 (1969) phenyl 2-pyridinyl ketone, O-di(m)ethylaminoethyl oxime; 4-methoxyphenyl 2-thienyl ketone, O-dimethylaminoethyl oxime; and phenyl 2-picolinyl ketone, O-dimethylaminoethyl oxime have been described, which compounds showed anti-androgenic activity, but the effective dose was very close to the toxic dose.

It has now been found that certain oxime ethers derived from heterocyclic ketones possess anti-ulcer activity in the gastro-intestinal tract, e.g. by inhibition of gastric acid secretion and/or stimulation of mucus formation, and that these compounds and pharmaceutical compositions containing them may be used in the treatment and/or prophylaxis of disorders of the gastro-intestinal tract.

The invention provides a compound of the formula (I):

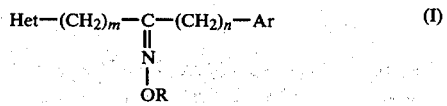

or a pharmaceutically acceptable salt thereof, wherein:
Het is a monocyclic heteroaromatic group containing two hetero atoms at least one of which is nitrogen, or a bicyclic heteroaromatic group containing one or two hetero atoms at least one of which is nitrogen, or such a mono- or bicyclic group substituted by one or more halogen atoms or $C_{1-6}$ alkyl or $C_{1-6}$ alkoxy groups,
Ar is a phenyl or a 5- or 6-membered monocyclic heteroaromatic group, or such a group substituted by one or more halogen atoms or $C_{1-6}$ alkyl or $C_{1-6}$ alkoxy groups,
R is a $C_{1-3}$ alkyl, $C_{3-4}$ alkenyl, $C_{3-4}$ alkynyl, cyano $C_{1-3}$ alkyl, a carbamidoalkyl group with the formula $-(CH_2)_pC(O)NR^1R^2$, wherein p=1 or 2, $R^1$ and $R^2$ are each hydrogen or $C_{1-3}$ alkyl, or $R^1$ and $R^2$ together with the nitrogen atom to which they are attached form a 5- or 6-membered heterocyclic ring in which another hetero atom may be present, or an aminoalkyl group with the formula $-(CH_2)_qNR^3R^4$, wherein q=2 or 3, $R^3$ and $R^4$ are each hydrogen or $C_{1-3}$ alkyl, or $R^3$ and $R^4$ together with the nitrogen atom to which they are attached form a 5- or 6-membered heterocyclic ring in which another hetero atom may be present,
m and n are each 0 or 1, with the proviso that m+n is not 2;
or an N-oxide or a pharmaceutically acceptable salt thereof.

One sub-class of the compounds of formula (I) is that in which Het is a pyrazinyl, pyrimidinyl, imidazolyl, imidazo-pyridinyl, indolyl, indolizinyl, quinoxalinyl, quinazolinyl, phthalazinyl, quinolinyl, isoquinolinyl, benzimidazolyl, benzoxazolyl, benzothiazolyl or thiazolyl group, or such a group substituted by one or more halogen atoms or $C_{1-6}$ alkyl or $C_{1-6}$ alkoxy groups, and Ar and R are as defined above, or an N-oxide of such group or a pharmaceutically acceptable salt of said compound or said N-oxide.

Another sub-class of the compounds of formula (I) is that in which Het is a pyrazinyl, pyrimidinyl, imidazolyl, imidazo-pyridinyl, indolyl, indolizinyl, quinoxalinyl, quinazolinyl, phthalazinyl, quinolinyl, isoquinolinyl, benzimidazolyl, benzoxazolyl or benzothiazolyl group, or such a group substituted by one or more halogen atoms or $C_{1-6}$ alkyl or $C_{1-6}$ alkoxy groups, and Ar and R are as defined above, or an N-oxide thereof or an addition salt of said compound or said N-oxide.

The compounds of formula (I) may be substituted or unsubstituted in Het, as described. However, it is believed that a preferred class of such compounds for their utility is that in which Het is unsubstituted in the ring carbon atoms.

Examples of suitable Het groups are pyrazinyl, 2-, 4- or 5-pyrimidinyl, 2-imidazolyl, 1-methyl-2-imidazolyl, 2- or 3-imidazo[1,2-a]-pyridinyl, 2-indolyl, 2-methyl-3-indolizinyl, 2-quinoxalinyl, 2- or 4-quinazolinyl, 1-phthalazinyl, 2-quinolinyl, 2-benzimidazolyl, 2-benzoxazolyl, 2-benzothiazolyl and 2-thiazolyl.

Het is preferably Het' where Het' is pyrazinyl, 2-imidazolyl, 1-methyl-2-imidazolyl or 2- or 3-imidazo[1,2-a]pyridinyl.

Ar is preferably Ar' where Ar' is phenyl, 2- or 4-tolyl, 4-chlorophenyl, 4-methoxyphenyl, 2- or 3-thienyl, 2-furyl or 2-pyridinyl, of which phenyl and 2-thienyl are most preferred.

R is preferably R' where R' is methyl, ethyl, n-propyl, allyl, propargyl, cyanomethyl, dimethylaminoethyl or dimethylaminopropyl, of which $C_{1-3}$ alkyl, particularly methyl, and dimethylaminopropyl are most preferred.

Preferably, m and n are zero. If, however, n is one, the preferred meaning of Ar is phenyl.

The pharmaceutically acceptable salts include the acid addition salts and quaternary addition salts. Among the therapeutically appropriate acids for the formation of addition salts are inorganic acids, such as hydrochloric acid, hydrobromic acid, sulphuric acid, nitric acid and phosphoric acid, and organic acids such as citric acid, acetic acid, oxalic acid, maleic acid, fumaric acid, lactic acid, succinic acid, tartaric acid and methanesulphonic acid, of which hydrochloric acid, sulphuric acid, maleic acid and methanesulphonic acid are preferred.

It will be realized that each compound of formula (I) may exist in two different forms (E and Z-isomer). Both such forms are included within this invention. The compounds of the invention, as represented by formula (I), include free base and addition salt forms, separated isomeric forms and mixtures thereof.

Particularly preferred compounds within the formula (I) are of formula (I)':

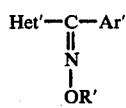     (I)' wherein Het' is pyrazinyl, 2-imidazolyl, 1-methyl-2-imidazolyl or 2- or 3-imidazo[1,2-a]pyridinyl, Ar' is phenyl or 2-thienyl and R' is methyl or dimethylaminopropyl.

Preferably, when Het' is pyrazinyl, R' is dimethylaminopropyl and when Het' is 2-imidazolyl or 1-methyl-2-imidazolyl, R' is methyl.

Especially preferred compounds within the formula (I)' are: phenyl pyrazinyl ketone, O-3-N,N-dimethylaminopropyl oxime, 2-imidazolyl phenyl ketone, O-methyl oxime (E and Z-isomer), and 1-methyl-2-imidazolyl phenyl ketone, O-methyl oxime.

The compounds of the invention can be prepared according to methods which are known per se for the preparation of this type of compounds, or methods analogous thereto.

A suitable method for the preparation of a compound of formula (I) comprises the reaction of a compound of formula (II):

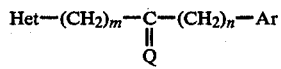     (II)

wherein Het, Ar, m and n are as defined in relation to formula (I) and C=Q is a carbonyl group or a protected carbonyl group, with a O-substituted hydroxylamine derivative of formula (III):

     (III)

or a salt thereof, wherein R is as defined in relation to formula (I).

Suitable protected carbonyl groups are, for example, ketals and oximes. The preferred meaning of Q is oxygen. If Q is an alkylenedioxy group, it is preferably ethylenedioxy.

The reaction may be carried out under reaction conditions which are commonly used for this type of reaction. Preferably the reaction is carried out in a solvent, such as an alcohol, dioxane, dimethyl formamide, tetrahydrofuran or pyridine. Usually, the reaction temperature will be between room temperature and the boiling temperature of the reaction mixture.

The compound (III) is preferably added in the form of its acid salt, preferably its hydrochloride, to compound (II), which is preferably dissolved in pyridine.

A further suitable method for the preparation of a compound of formula (I) comprises the reaction of a compound of formula (IV):

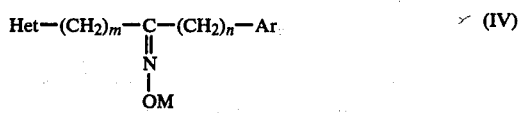     (IV)

wherein Het, Ar, m and n are as defined in relation to formula (I) and M is a hydrogen or an alkali metal atom, with a compound of formula (V):

     (V)

wherein R is as defined in relation to formula (I) and Y is a suitable leaving group, such as a chloride, bromide, iodide or tosyloxy group.

The reaction may be carried out in a conventional solvent, such as methanol, ethanol, acetone, methyl ethyl ketone, dioxane, dimethylglycol ether or dimethyl formamide. If in formula (IV) M represents a hydrogen atom, it may be useful to add an acid binding agent to the reaction mixture. Suitable acid binding agents are, for example, alkali metal hydrides, hydroxides, carbonates and alkoxides, tertiary amines, pyridine and the like. The reaction conditions are as commonly used for this type of reaction. Usually, the reaction temperature will be between room temperature and the boiling temperature of the reaction mixture.

The conversion of the oxime compound (IV) into compound (I) is usually effected by alkylation with an alkyl, alkenyl, alkynyl, carbamidoalkyl, cyanoalkyl or (tert-amino)alkyl halide, such as the chloride, bromide or iodide, in the presence, for instance, sodium hydride, an alkali metal hydroxide or alkoxide, preferably sodium methoxide, dissolved in a suitable solvent, preferably dimethyl formamide or methyl alcohol.

Generally, the preferred method of preparing any particular compound of formula (I) will depend to some extent on the compound itself.

It will be clear to those skilled in the art that, in a number of cases, certain reaction steps described may be carried out in a different sequence or simultaneously or without isolating intermediates, and these possibilities are all included in the invention. For example, the introduction of the group R in compound (I) according to the reaction of compound (II) with compound (III) may also be carried out by reacting compound (II) with a compound of formula (VI):

     (VI)

wherein Z is a group replaceable by or convertible into R, R being as hereinbefore defined. The compound of formula (VII) thus obtained:

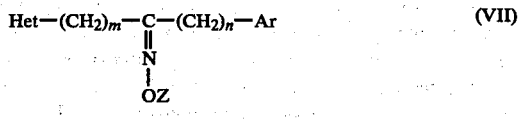     (VII)

wherein Het, Ar, Z, m and n are as hereinbefore defined, can then be converted to the compound of formula (I).

The N-oxides of the compounds of formula (I) are preferably prepared by reacting a compound of formula (I) with a peroxide, for example, hydrogen peroxide, benzoyl peroxide, or a similar compound, of which hydrogen peroxide is preferred. The reaction is preferably carried out in an inert solvent, such as, for example, acetic acid, propionic acid, and the like, at temperatures generally ranging between 50° C. and 90° C.

The N-oxides can also be prepared by reacting a compound of formula (II), wherein Het is the N-oxide of the previously defined hetero group (instead of the hetero group itself), with a hydroxylamine derivative of formula (III), in the manner hereinbefore described.

The compounds of formula (I) (and their N-oxides and/or addition salts) are believed to be novel and as such form an important aspect of the invention.

The intermediate compounds with formulae (II) and (IV) have been frequently described in the literature or can be prepared by analogous methods.

The invention also provides a pharmaceutical composition comprising a compound of the formula (I) (or a N-oxide and/or addition salt) together with a pharmaceutically acceptable carrier or diluent.

The formulation of the pharmaceutical composition will depend on the nature of the activity shown by the chosen compound of the formula (I), and on other factors such as a preference in a particular area of therapy for a particular mode of administration.

The compositions may be, for example, in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions of this invention may be in the form of an aerosol for oral administration, or a microfine powder for insulation. As is common practice, the compositions will usually be accompanied by written or printed directions for use in the medical treatment concerned.

It will of course be realized that the precise dosage used in the treatment of any of the hereinbefore described disorders will depend on the actual compound of formula (I) (or N-oxide or addition salt thereof) used, and also on other factors such as the seriousness of the disorder being treated. Broadly, the dose may vary from about 100 mg up to about 25 g per day per patient.

The invention also provides a method of treatment and/or prophylaxis of gastric disorders in human beings which comprises the administration to the sufferer of an effective amount of a compound of formula (I) (or N-oxide or addition salt thereof), or of a composition of the invention. The "effective amount" will of course vary with factors such as severity of the ulceration, the weigth of the sufferer and the specific compound of the formula (I) used.

The following Examples illustrate the preparation of compounds of formula (I) and their pharmacological properties.

EXAMPLE 1

Phenyl pyrazinyl ketone, O-methyl oxime

Phenyl pyrazinyl ketone (18.4 g) and O-methylhydroxylamine hydrochloride (12 g) dissolved in 200 ml of pyridine were refluxed for 8 hours. Pyridine was distilled off under reduced pressure, and the residue was treated with chloroform and water. The chloroform layer was separated and dried over magnesium sulphate. Evaporation of the solvent and successive crystallization of the residue from petroleum ether (b.p. 40°–60° C.) afforded the title compound as a mixture of the E and Z-isomers (18.0 g).

The pure Z-isomer was obtained by fractional crystallization, m.p. 72°–73° C.; (1).

In a similar manner, the following compounds were prepared (the isomers were separated by column chromatography or fractional crystallization):

4-chlorophenyl pyrazinyl ketone, O-methyl oxime, m.p. 87°–89° C. (Z-isomer); (2).

4-chlorophenyl pyrazinyl ketone, O-methyl oxime, m.p. 54°–55° C. (E-isomer); (3).

4-methoxyphenyl pyrazinyl ketone, O-methyl oxime, m.p. 90°–93° C. (E-isomer); (4).

4-methoxyphenyl pyrazinyl ketone, O-methyl oxime, m.p. 70.5°–72° C. (Z-isomer); (5).

4-methylphenyl pyrazinyl ketone, O-methyl oxime, m.p. 70°–71° C. (Z-isomer); (6).

4-fluorophenyl pyrazinyl ketone, O-methyl oxime, m.p. 89°–90° C. (Z-isomer); (7).

4-fluorophenyl pyrazinyl ketone, O-methyl oxime, m.p. 77°–79° C. (E-isomer); (8).

2-methyl-3-indolizinyl phenyl ketone, O-methyl oxime, oil; (9).

2-imidazo[1,2-a]pyridinyl phenyl ketone, O-methyl oxime, m.p. 101°–102° C. (E-isomer); (10).

2-imidazo[1,2-a]pyridinyl phenyl ketone, O-methyl oxime, m.p. 111°–112° C. (Z-isomer); (11).

3-imidazo[1,2-a]pyridinyl phenyl ketone, O-methyl oxime, m.p. 112°–113° C. (E-isomer); (12).

3-imidazo[1,2-a]pyridinyl phenyl ketone, O-methyl oxime, m.p. 95°–97° C. (Z-isomer); (13).

2-methyl-3-imidazo[1,2-a]pyridinyl phenyl ketone, O-methyl m.p. 200°–204° C.; oxime.HCl; (14).

2-phenyl-3-imidazo[1,2-a]pyridinyl phenyl ketone, O-methyl oxime, m.p. 147°–149° C. (E-isomer); (15).

2-benzothiazolyl phenyl ketone, O-methyl oxime, m.p. 75°–76° C.; (16).

2-imidazolyl phenyl ketone, O-methyl oxime, m.p. 188° C. (E-isomer); (17).

2-imidazolyl phenyl ketone, O-methyl oxime, m.p. 201° C. (Z-isomer); (18).

1-methyl-2-imidazolyl phenyl ketone, O-methyl oxime, m.p. 84°–85° C.; (19).

2-benzimidazolyl phenyl ketone, O-methyl oxime, m.p. 185° C. (dec.); (20).

phenyl 2-thiazolyl ketone, O-methyl oxime, m.p. 65°–66° C. (E-isomer); (21).

phenyl 2-thiazolyl ketone, O-methyl oxime.HBr m.p. 173°–175° C. (Z-isomer); (22).

2-furanyl pyrazinyl ketone, O-methyl oxime, oil; (23).

EXAMPLE 2

Phenyl pyrazinyl ketone, O-cyanomethyl oxime; (24)

Phenyl pyrazinyl ketone oxime (8.0 g) was stirred in 100 ml of dimethyl formamide containing 2.0 g of a 50% dispersion of sodium hydride in oil, for 0.5 hours at room temperature. Chloroacetonitrile (2.7 g) was added. The reaction mixture was stirred for 1 hour. The greater part of the dimethylformamide was evaporated under reduced pressure and the residue was treated with ether and water. The ether layer was separated and dried over magnesium sulphate. The product was recrystallized from a mixture of ether and petroleum ether (40°–60° C.), yielding pure phenyl pyrazinyl ketone, O-cyanomethyl oxime (5.6 g, m.p. 87°–89° C.).

In a similar manner the following compounds were prepared:

phenyl pyrazinyl ketone, O-allyl oxime, oil; (25).

phenyl pyrazinyl ketone, O-propargyl oxime, m.p. 62°–64° C.; (26).

phenyl pyrazinyl ketone, O-3-N,N-dimethylaminopropyl m.p. 125°–126° C.; oxime.1 maleic acid; (27).

phenyl pyrazinyl ketone, O-2,N,N-dimethylaminoethyl m.p. 124.5°–125° C.; oxime.1 maleic acid; (28).

3-imidazo[1,2-a]pyridinyl phenyl ketone, O-3-N,N-dimethylaminopropyl m.p. 138°–139° C.; oxime.½ fumaric acid; (29).

phenyl 2-quinolinyl ketone, O-3-N,N-dimethylaminopropyl m.p. 137°–139° C.; oxime.1 fumaric acid; (30).

2-imidazolyl phenyl ketone, O-3-N,N-dimethylaminopropyl oxime m.p. 102.5° C.; (31).

1-methyl-2-imidazolyl phenyl ketone, O-3-N,N-dimethylaminopropyl oil; oxime; (32).

2-benzothiazolyl phenyl ketone, O-3-N,N-dimethylaminopropyl m.p. 178°–179° C. oxime.1 fumaric acid; (33).

phenyl 2-thiazolyl ketone, O-3-N,N-dimethylaminopropyl m.p. 88°–89° C. (E-isomer); oxime.1 fumaric acid; (34).

Pharmacological Data

1. Effects on Gastric Secretion, in the Pyloric Ligated Rat.

The method as described by Shay et al. (Gastroenterol. 26, 906 (1945)) was used. After overnight starvation, the pylorus was ligated under halothane anaesthesia, and the compound under test or vehicle only administered intraduodenally and the rats allowed to recover. They were sacrificed three hours later and the gastric juice removed. After measurement of the volume of secretion, its hydrogen ion concentration [H+] was determined by titration with 0.05 n NaOH to pH 7. Groups of 4–6 animals were used for each treatment and the inhibitory effects of the compound were ascertained by comparison of the mean values obtained with those from a simultaneously set up control group of animals which received vehicle only. Students 't' test was applied for significance between groups. The mean values for % inhibition obtained for a number of experiments are shown in the following Table 1, the dosage being 100 mg/kg i.d.

2. Anti-ulcer activity

This was assessed by the inhibition of indomethacin induced gastric damage in the rat according to the method of Elegbe (Israeli J. Med. Sci. 10, 1451 (1974)).

Rats were starved overnight, given indomethacin subcutaneously (15 mg/kg) and sacrificed 5 hours later. Stomachs were inflated with 0.9% saline, cut along the greater curvature, pinned out and scored for gastric damage by the following system:

Score 1–3 according to the degree of erythema and slight haemorrhage.

Score 4–6 according to the degree of mucosal erosion.

Score 7–9 according to the depth of gastric damage. Groups of 7 rats were used for each treatment level of the compound under test and a similar group receiving vehicle only was set up on each occasion of testing. Compound or vehicle was administered orally 30 minutes prior to, and at 2 hours after, dosing with indomethacin. Mean values per treatment were obtained using the above scoring system and the Mann Witney test applied for significance between such values. The mean inhibition of gastric damage from a number of experiments is shown in the following Table 2; the dosage being 100 mg/kg orally.

| Compound No. | Table 1 % Inhibition | | Table 2 % Inhibition |
|---|---|---|---|
| | Volume | [H+] | |
| 1 | 77 | 23 | 74* |
| 2 | 68 | 21 | 68 |
| 7 | 72 | | 96 |
| 8 | 72 | | 96 |
| 9 | 83 | 52 | |
| 10 | 66 | 23 | 89* |
| 11 | 77 | | 67* |
| 12 | 55 | 25 | 61 |
| 14 | 59 | 23 | 78 |
| 17 | 55 | 26 | 100 |
| 18 | 87 | | 91 |
| 19 | 69 | 49 | 91 |
| 20 | | | 78 |
| 21 | 57 | | 89 |
| 22 | 68 | | 78 |
| 23 | 67 | | 98 |
| 24 | | | 93 |
| 25 | 87 | 27 | 56 |
| 26 | | | 53 |
| 27 | 67 | 49 | 92 |
| 28 | 56 | 59 | |
| 29 | | | 75 |
| 30 | 72 | 37 | 79 |
| 31 | 80 | 72 | 56 |
| 32 | 83 | 41 | |
| 33 | 55 | 38 | 62 |

-continued

Table 1

| Compound No. | % Inhibition | | Table 2 |
| | Volume | [H+] | % Inhibition |
| --- | --- | --- | --- |
| 34 | 82 | 42 | |

*50 mg/kg

What we claim is:

1. A compound of the formula:

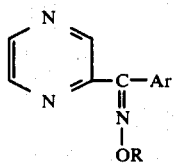

or an N-oxide thereof, or a pharmaceutically acceptable salt of said compound or said N-oxide, wherein:

Ar is phenyl, thienyl, furyl or pyridinyl, said phenyl being unsubstituted or mono substituted by halogen, $C_{1-6}$ alkyl or $C_{1-6}$ alkoxy, R is $C_{1-3}$ alkyl, $C_{3-4}$ alkenyl, $C_{3-4}$ alkynyl, cyano $C_{1-3}$ alkyl or aminoalkyl with the formula $-(CH_2)_q NR^3R^4$, wherein q is 2 or 3, $R^3$ and $R^4$ are each hydrogen or $C_{1-3}$ alkyl.

2. A compound according to claim 1, wherein Ar is phenyl, 2- or 4-tolyl, 4-chlorophenyl, 4-methoxyphenyl, 2- or 3-thienyl, 2-furyl or 2-pyridinyl.

3. A compound according to claim 1, wherein R is methyl, ethyl, n-propyl, allyl, propargyl, cyanomethyl, dimethylaminoethyl or dimethylaminopropyl.

4. A compound according to claim 1, wherein Ar is phenyl or 2-thienyl, and R is $C_{1-3}$ alkyl or dimethylaminopropyl, or a pharmaceutically acceptable salt thereof.

5. The compound according to claim 1 which is phenyl pyrazinyl ketone, O—3—N,N-dimethylaminopropyl oxime, or a pharmaceutically acceptable salt thereof.

6. A compound according to claim 1 or 5, which is substantially entirely in the form of the E or the Z isomer.

7. A pharmaceutical composition for treatment of disorders of the gastro-intestinal tract, which comprises a therapeutically effective amount of a compound according to claim 1, or an N-oxide thereof, or a pharmaceutically acceptable salt of said compound or said N-oxide, in association with a pharmaceutically acceptable diluent or carrier.

8. A method of treating disorders of the gastro-intestinal tract of a mammal which comprises administering to said mammal a therapeutically effective amount of a compound according to claim 1, or an N-oxide thereof, or a pharmaceutically acceptable salt of said compound or said N-oxide.

* * * * *